United States Patent [19]

Rees

[11] 4,104,522
[45] Aug. 1, 1978

[54] APPARATUS FOR MEASURING THE WEIGHT PER UNIT LENGTH OF A CIGARETTE ROD

[75] Inventor: Peter William Rees, Bexley Heath, England

[73] Assignee: Measurex Corporation, Cupertino, Calif.

[21] Appl. No.: 776,826

[22] Filed: Mar. 14, 1977

[51] Int. Cl.² .............................. G01N 23/02
[52] U.S. Cl. .................. 250/359; 131/21 B; 131/22 R; 250/308; 250/360
[58] Field of Search .......... 250/308, 359, 360; 131/21 B, 22 R

[56] References Cited

U.S. PATENT DOCUMENTS

| | | | |
|---|---|---|---|
| 2,952,262 | 9/1960 | Pocock et al. | 131/21 B |
| 2,954,775 | 10/1960 | Radley et al. | 250/308 X |
| 3,253,149 | 5/1966 | Wilson | 250/308 |

Primary Examiner—Archie R. Borchelt
Attorney, Agent, or Firm—Ronald L. Yin

[57] ABSTRACT

An apparatus for measuring the weight per unit length of a cigarette rod has a radioactive source to one side of the rod and a detector to the other side of the rod. The source emits a beam of radiation through the rod to the detector. Guide tubes, having air ducts, are located on both sides of the beam. Pressurized air is introduced into the tubes via the air ducts to maintain the rod centrally within the tubes.

5 Claims, 4 Drawing Figures

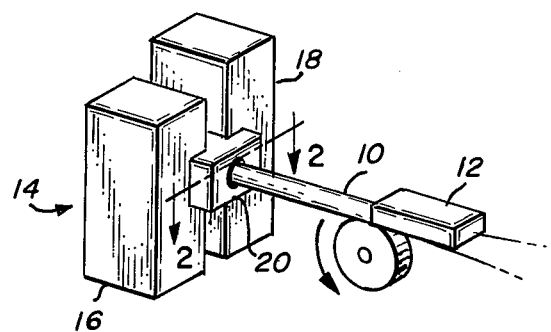
Fig. 1
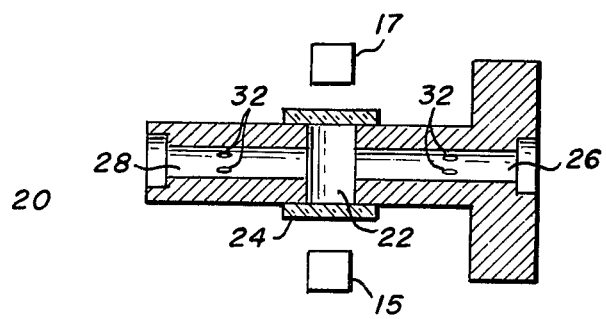
Fig. 2
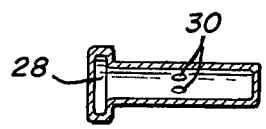 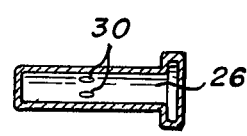
Fig. 3  Fig. 4

APPARATUS FOR MEASURING THE WEIGHT PER UNIT LENGTH OF A CIGARETTE ROD

BACKGROUND OF THE INVENTION

The present invention relates to an apparatus for measuring the weight per unit length of a cigarette rod in a cigarette-making machine, and more particularly to such an apparatus which has means for centrally positioning the rod to effect an accurate measurement.

In a cigarette-making machine, tobacco is formed within a continuous tube of paper to give a rod which is cut into individual cigarettes. Measurement of the cigarette rod weight per unit length is made at the continuous rod stage so that an indication can be obtained for control purposes and automatic weight control and inspection and other measurements of weight variation can be effected. The weight measurement is made by passing radiation from a radio-active isotope through the rod to a radiation detector, the degree of radiation absorption being an indication of average weight. In practice, the radiation source must be small and the cigarette rod must run close to the source. Minor variations in the position of the rod affect the radiation transmission and give rise to errors in weight determination. Generally, the rod is supported in a tube which may have a thin-walled window or a space at the radiation area. The tube should be small in diameter to restrict lateral movement of the rod. However, the rod may have irregularities in shape or diameter which cause the rod to snag and tear on small guide tubes. Guide tubes at present are therefore larger than is required for very accurate weight measurement. The present invention seeks to overcome this difficulty.

SUMMARY OF THE INVENTION

An apparatus for measuring the weight per unit length of a cigarette rod in a cigarette making machine comprises a radioactive source to one side of the rod capable of emitting a radiation beam substantially in a radial direction through the rod. A radioactive detector is to the other side of the rod capable of measuring the amount of radiation passing through the rod. A first guide means, containing a plurality of ducts, is to one side of the beam. Air, under pressure, is introduced into the ducts to form an air bearing between the first guide means and the rod. A second guide means also containing a plurality of ducts is to the other side of the beam. Similarly, air, under pressure, is introduced into the ducts to form an air bearing between the second guide means and the rod.

BRIEF DESCRIPTION OF THE DRAWINGS

FIG. 1 is a schematic perspective view of the apparatus of the present invention.

FIG. 2 is a cross-sectional view taken along 2—2 of the guide housing of FIG. 1.

FIG. 3 is a cross-sectional view of the rear guide means of FIG. 2.

FIG. 4 is a cross-sectional view of the front guide means of FIG. 2.

DETAILED DESCRIPTION OF THE DRAWINGS

Referring to FIG. 1, there is shown a cigarette rod 10 issuing continuously from a heater station 12 of a cigarette making machine. A strip of paper has been folded around a column of tobacco in a tube (not shown) to make rod 10. The heating station 12 is for heating the rod 10 to cure the gum which sticks to the paper. The rod 10 passes into the apparatus 14 of the present invention. Afterwards, the rod 10 passes into a cutting station (not shown) where cigarettes are cut from the rod 10.

The apparatus 14 comprises a source housing 16, a detector housing 18 and a guide housing 20. The source housing 16 holds a radio-active source 15 (shown in FIG. 2), which is typically of strontium 90. The detector housing 18 contains a radio-active detector 17 (shown in FIG. 2), which is typically an ionization chamber. The cigarette rod 10 passes into a guide housing 20, which is between the source housing 16 and the detector housing 18. In particular, the rod 10 passes between the source 15 and the detector 17. The source 15 emits a beam of radiation substantially in a radial direction through the rod 10 and onto the detector 17. The rod 10 shields a certain amount of radiation from the source 15 to the detector 17. The level of radiation received by the detector 17 is a measure of the weight per unit length of the rod 10. Control of the tobacco filling to maintain a pre-determined weight is possible with knowledge of the level of radiation received.

The guide housing 20 is shown in greater detail in FIG. 2. The guide housing 20 has a chamber 22 where the radiation beam from the source 15 is passed through the rod 10 and into the detector 17. Chamber 22 has a window 24 for allowing radiation to pass to the detector 17. A front guide 26 to one side of the beam leads the rod 10 to a measuring position, i.e., where the beam from the source 15 impinges the rod 10, in chamber 22. A rear guide 28 to the other side of the beam leads the rod 10 away from the measuring position in chamber 22.

To restrict the movement of rod 10 in the measuring position and therefore to control the accuracy of the measurement, the front guide 26 is tubular in shape (shown in cross-section view in FIG. 4). Similarly, the rear guide 28 is also tubular in shape (shown in cross-sectional view in FIG. 3). The guides 26 and 28 are generally made of stainless steel and are of such a diameter as to accomodate rod 10 with a small clearance.

Chamber 22 is sealed by two sheets of radiation-transparent foil and the guides 26 and 28 are sealed in place by means of 'O'-ring seals (not shown). Holes 30 supply air under pressure of between 1 and 2 atmospheres above atmospheric pressure. Holes 30 are aligned with holes 32 in guides 26 and 28 and thus the pressurized air is supplied to the interior of guides 26 and 28, so forming an air bearing between each of the guides and the rod 10. The pressurized air maintains the rod 10 centrally within the guides 26 and 28 and thus maintains the rod 10 at the required position during weight measurement. Air escapes via the open ends of the guides 26 and 28 and also via the chamber 22 which is vented to atmosphere.

In accordance with a preferred feature of the present invention, the air pressure applied to holes 30 is measured and is used to give an indication of rod cross-section, or firmness, or both, since these factors will affect the air pressure.

In another preferred embodiment a flow of air is provided in the chamber 22 in order to prevent moisture condensation and the build-up of dust and particles in the measuring region. Such air is of low volume and pressure and is not to be confused with the air required in accordance with the present invention to provide air bearings.

The present invention is not restricted to the details of the above-described embodiment. For example, in an alternative arrangement the chamber 22 is sealed and the high-pressure air for the air bearing is introduced through a duct in the chamber 22. The air escapes in both directions along the clearance between rod 10 and the respective guides 26 and 28 to atmosphere.

In another arrangement, the guides 26 and 28 form part of an integral guide tube having a thin-walled section at the measuring position. The wall at this point is thin enough to allow the passage of the radiation.

Under some circumstances it is possible to obtain improved performance by imparting a swirling motion to the air with appropriately directed ducts. Also, the air is best directed along the direction of travel of the rod 10 so that ducts for the introduction of the air may be inclined both axially and forwardly.

Swirling motion of the air may be induced or enhanced by shallow helical ribs or grooves formed in the inside faces of the guides 26 and 28. The guides 26 and 28 can be tapered to enhance flow characteristics.

The use of an air bearing of this kind allows the cigarette rod 10 to be accurately positioned centrally within guide tubes. Thus, accurate measurements can be made.

What is claimed is:

1. An apparatus for measuring the weight per unit length of a cigarette rod in a cigarette making machine, said apparatus comprises:
   a radio-active source to one side of said rod, said source capable of emitting a radiation beam substantially in a radial direction through the rod;
   a detector to other side of said rod, said detector capable of receiving said radiation;
   first means for guiding said rod located to one side of said beam, said means having a plurality of ducts for introducing air under pressure to form an air bearing between said means and said rod; and
   second means for guiding said rod located to other side of said beam, said means having a plurality of ducts for introducing air under pressure to form an air bearing between said means and said rod.

2. The apparatus of claim 1 wherein said first means is a first guide tube.

3. The apparatus of claim 2 wherein said second means is a second guide tube.

4. The apparatus of claim 3 wherein air is introduced into said first guide tube at about between one and two atmospheres above atmospheric pressure.

5. The apparatus of claim 4 wherein air is introduced into said second guide tube at about between one and two atmospheres above atmospheric pressure.

* * * * *